United States Patent [19]

Lilburn

[11] 4,196,090
[45] Apr. 1, 1980

[54] HYDROCARBYLPOLY(OXYALKYLENE) AMINOPHOSPHORYLAMIDO ESTERS AND LUBRICATING OIL COMPOSITIONS CONTAINING THE ESTERS

[75] Inventor: Jennifer E. Lilburn, Berkeley, Calif.
[73] Assignee: Chevron Research Company, San Francisco, Calif.
[21] Appl. No.: 939,305
[22] Filed: Sep. 5, 1978
[51] Int. Cl.$^2$ .................. C10M 1/36; C10M 1/46; C07F 9/24
[52] U.S. Cl. .................. 252/49.9; 260/950; 260/951; 544/157; 544/337; 546/21; 548/351
[58] Field of Search .............. 252/49.9; 260/950, 951; 544/157, 337; 546/21; 548/351

[56] References Cited

U.S. PATENT DOCUMENTS 3,374,072   3/1968   Deffner .................. 44/58

FOREIGN PATENT DOCUMENTS 583579   9/1959   Canada .................. 260/950

*Primary Examiner*—W. J. Shine
*Attorney, Agent, or Firm*—D. A. Newell; S. R. LaPaglia

[57] ABSTRACT

Hydrocarbylpoly(oxyalkylene) aminophosphorylamido esters are monoesters and diesters of polyether alcohols and phosphoramidic acids. The esters find use as lubricating oil additives which impart lubricity to the oil.

13 Claims, No Drawings

HYDROCARBYLPOLY(OXYALKYLENE) AMINOPHOSPHORYLAMIDO ESTERS AND LUBRICATING OIL COMPOSITIONS CONTAINING THE ESTERS

BACKGROUND OF THE INVENTION

Current limitations on the use of phosphorus in certain fuels for internal combustion engines provide the inpetus for seeking means of lowering the phosphorus content of lubricating oils while maintaining or improving the lubricity and other properties imparted to the oil by phosphorus-containing additives. Such phosphorus-containing additives, in addition to the widely used zinc dithiophosphates, include the amine salts of polyether phosphoryl esters disclosed in U.S. Pat. Nos. 3,547,820, 3,310,489, 3,558,489 and 3,567,636. Amidophosphates, U.S. Pat. No. 3,374,072, and tri(alkoxyalkyl) phosphates, U.S. Pat. No. 3,009,072, have found use in providing special properties to fuel compositions.

SUMMARY OF THE INVENTION

The hydrocarbylpoly(oxyalkylene) aminophosphorylamido esters are amides or phosphoric acid, $P(O)(OH)_3$, and a polyamine, and esters of phosphoric acid and a hydrocarbylpoly(oxyalkylene) alcohol. The esters include both monoesters (i.e., monoamides and diamides) and diesters (i.e, monoamides). The polyamine from which said aminophosphorylamido ester is derived contains from 2 to about 12 nitrogen atoms and from 2 to about 40 carbon atoms. The hydrocarbyl group in said hydrocarbylpoly(oxyalkylene) alcohol from which said aminophosphorylamido ester is derived contains from 1 to about 30 carbon atoms. It has been found that improved lubricating oil compositions comprise a major amount of an oil of lubricating viscosity and about 0.001-20 weight percent of a hydrocarbylpoly(oxyalkylene) aminophosphorylamido ester. Not only do the lubricating oil additives of this invention have many of the attributes of the zinc dithiophosphates, but such attributes are provided with relatively low phosphorus present in the lubricating composition and without zinc or other metal.

DETAILED DESCRIPTION OF THE INVENTION

The hydrocarbylpoly(oxyalkylene) aminophosphorylamido esters of the present invention are amides and esters of phosphoric acid, $P(O)(OH)_3$. The ester moieties of the aminophosphorylamido ester are derived from a hydrocarbylpoly(oxyalkylene) alcohol, while the aminoamide moieties of the aminophosphorylamido ester are derived from polyamines. The aminophosphorylamido esters include both monoesters (i.e., monoamides and diamides) and diesters (i.e., monoamides) of phosphoric acid. The monoesters have average molecular weights of from about 600 to 5000 and the diesters have average molecular weights from about 1000 to 10,000. In the terminology suggested by Chemical Abstracts Service (Chemical and Engineering News, Vol. 30, pp. 4515-22, 1952), the diesters of the present invention are diesters of a phosphoramidic acid, i.e., diesters of

The particular diesters of the present invention are esters of polyether alcohols and are representable as

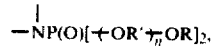

wherein R is a hydrocarbyl group of from 1 to 30 carbon atoms, —OR'— is an oxyalkylene group and n is a integer. The monoesters of the present invention are monoesters of phosphordiamidic acid, i.e., monoesters of

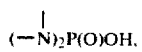

and include monoesters of a phosphorcyclodiamidic acid, i.e., include monoesters of

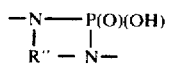

wherein R" is ethylene or propylene. The monoesters are representable as

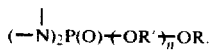

In each instance the amido nitrogen atoms are bound to phosphorus and the remainder of the aminoamide moiety.

Preferred Aminoamide Component

The aminoamide moiety of the hydrocarbylpoly(oxyalkylene) aminophosphorylamido esters is preferably derived from a polyamine having from 2 to about 12 amine nitrogen atoms and from 2 to about 40 carbon atoms. The polyamine is preferably reacted with a hydrocarbylpoly(oxyalkylene) chlorophosphoryl ester to produce the hydrocarbylpoly(oxyalkylene) aminophosphorylamido ester of the present invention. The chlorophosphoryl ester is itself derived from phosphoryl trichloride, $P(O)Cl_3$, by reaction with a poly(oxyalkylene) alcohol. The polyamine, encompassing diamines, provides the product aminophosphorylamido ester with, on the average, at least about 1 basic nitrogen atom per aminophosphorylamido ester molecule, i.e., a nitrogen atom titratable by a strong acid. The polyamine preferably has a carbon-to-nitrogen ratio from about 1:1 to about 10:1.

The polyamine may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like "lower alkyl" or "lower alkoxy", means a group containing from 1 to about 6 carbon atoms.

"Hydrocarbyl", as used in describing all the components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, diethyleneoxyethyl, triethyleneoxyethyl, tetraethyleneoxyethyl, diethyleneoxyhexyl, etc. The aforementioned acyl groups (C) are such as propionyl, acetyl, etc. The more preferred substituents are hydrogen, $C_1$-$C_6$ alkyls and $C_1$-$C_6$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and poly-substituted polyamines with substituent groups situated at equivalent and/or inequivalent atoms.

The more preferred polyamine finding use within the scope of the present invention is a polyalkylenepolyamine, including alkylenediamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethylpropylene, trimethylene, 1,3,2-hydroxypropylene, etc. Examples of such polyamines include ethylenediamine, diethylenetriamine, di(trimethylene)triamine, dipropylenetriamine, triethylenetetraamine, tripropylenetetraamine, tetraethylenepentamine, and pentaethylenehexamine. Such amines encompass isomers such as branched-chain polyamines and the previously-mentioned substituted polyamines, including hydroxy- and hydrocarbyl-substituted polyamines. Among the polyalkylene polyamines, those containing 2-12 amine nitrogen atoms and 2-24 carbon atoms are especially preferred, and the $C_2$-$C_3$ alkylenepolyamines are most preferred, in particular, the lower polyalkylenepolyamines, e.g., dipropylenetriamine, triethylenetetraamine, etc.

The aminoamide component of the poly(oxyalkylene) aminophosphorylamido ester also may be derived from heterocyclic polyamines, heterocyclic substituted amines and substituted heterocyclic compounds, wherein the heterocycle comprises one or more 5–6 membered rings containing oxygen and/or nitrogen. Such heterocyclic rings may be saturated or unsaturated and substituted with groups selected from the aforementioned (A), (B), (C) and (D). The heterocyclic compounds are exemplified by piperazines, such as 2-methylpiperazine, N-(2-hydroxyethyl)piperazine, 1,2-bis-(N-piperazinyl)ethane and N,N'-bis(N-piperazinyl)piperazine, 2-methylimidazoline, 3-aminopiperidine, 3-aminopyridine, N-(3-aminopropyl)morpholine, etc.

Typical polyamines that can be used to form the compounds of this invention by reaction with a poly(oxyalkylene) chlorophosphoryl ester include the following: ethylenediamine, 1,2-propylenediamine, 1,3-propylenediamine, diethylenetriamine, triethylenetetraamine, hexamethylenediamine, tetraethylenepentamine, dimethylaminopropylenediamine, N-(beta-aminoethyl)piperazine, N-(beta-aminoethyl)piperidine, 3-amino-N-ethylpiperidine, N-(beta-aminoethyl)morpholine, N,N'-di(beta-aminoethyl)piperazine, N,N-di(beta-amino-ethyl)imidazolidone-2, N-(beta-cyanoethyl)ethane-1,2-diamine, 1-amino-3,6,9-triazaoctadecane, 1-amino-3,6-diaza-9-oxadecane, N-(beta-aminoethyl)diethanolamine, N'-acetylmethyl-N-(beta-aminoethyl)ethane-1,2-diamine, N-acetonyl-1,2-propanediamine, N-(beta-nitroethyl)-1,3-propanediamine, 1,3-dimethyl-5-(beta-aminoethyl)hexahydrotriazine, N-(beta-aminoethyl)hexahydrotriazine, 5-(beta-aminoethyl)-1,3,5-dioxazine, 2-(2-aminoethylamino)ethanol, 2-[2-(2-aminoethylamino)ethylamino]ethanol.

The aminoamide component of the poly(oxyalkylene) aminophosphorylamido ester may also be derived from an amine-containing compound which is capable of reacting with a phosphorous compound to produce a hydrocarbylpoly(oxyalkylene) aminophosphorylamido ester.

In many instances, the amine used as a reactant in the production of the ester of the present invention is not a single compound, but a mixture in which one or several compounds predominate with the average composition indicated. For example, tetraethylenepentamine prepared by the polymerization of aziridine or the reaction of dichloroethylene and ammonia will have both lower and higher amine members, e.g., triethylenetetraamine, substituted piperazines and pentaethylenehexamine, but the composition will be mainly tetraethylenepentamine and the empirical formula of the total amine composition will closely approximate that of tetraethylenepentamine. Finally, in preparing the compounds of this invention, where the various nitrogen atoms of the polyamine are not geometrically equivalent, several substitutional isomers are possible and are encompassed within the final product. Methods of preparation of amines, amides and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirt-Othmer's "Encyclopedia of Chemical Technology", 2nd Ed., especially Vol. 2, pp. 99–116.

Preferred Poly(oxyalkylene) Component

The hydrocarbyl-terminated poly(oxyalkylene) polymers which are utilized in preparing the aminophosphorylamido ester of the present invention are monohydroxy compounds, i.e., alcohols, often termed monohydroxy polyethers, or "capped" poly(oxyalkylene) glycols and are to be distinguished from the poly(oxyalkylene) glycols (diols), or polyols, which are not hydrocarbyl-terminated, i.e., not capped. The hydrocarbyl-terminated poly(oxyalkylene) alcohols are produced by the addition of lower alkylene oxides, such as oxirane, ethylene oxide, 1,2-epoxyhexadecane, propylene oxide, the butylene oxides, or the pentylene oxides to the hydroxy compound ROH under polymerization conditions. Methods of production and properties of these polymers are disclosed in U.S. Pat. Nos. 2,841,479 and 2,782,240, and the aforementioned Kirk-Othmer's "Encyclopedia of Chemical Technology", Vol. 19, p. 507.

In the polymerization reaction, a single type of alkylene oxide may be employed, e.g., propylene oxide, in which case the product is a homopolymer, e.g., a poly(oxypropylene) alcohol. This alcohol may then be reacted with a $C_6$–$C_{32}$ 1,2-epoxide to make the hydrocarbylpoly(oxyalkylene) alcohol having at least one oxyalkylene unit with a $C_4$–$C_{30}$ side chain. Poly(oxyalkylene) copolymers are equally satisfactory starting materials for the addition of 1,2-epoxides, and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxide is copolymerized with other oxides, the higher reaction rate of ethylene oxide makes the preparation of random copolymers difficult. In either case, block copolymers can be prepared. Block copolymers are prepared by contacting the hydroxyl-containing compound with first one alkylene oxide, then the others in any order, or repetitively, under polymerization conditions. A particular block copolymer is represented by a polymer prepared by polymerizing propylene oxide on a suitable monohydroxy compound to form a poly(oxypropylene) alcohol and then polymerizing butylene oxide on the poly(oxypropylene) alcohol.

In general, the poly(oxyalkylene) polymers are mixtures of compounds that differ in polymer chain length. However, their properties closely approximate those of the polymer represented by the average composition and molecular weight.

The hydrocarbylpoly(oxyalkylene) moiety of the ester consists of one or more hydrocarbyl-terminated poly(oxyalkylene) polymers composed of oxyalkylene units containing from 2 to about 5 carbon atoms, and optionally including branched-chain $C_6$–$C_{32}$ oxyalkylene units having $C_4$–$C_{30}$ predominantly straight-chain alkyl substituents. The polymers are bound to phosphorus via oxygen linkages, and the poly(oxyalkylene) aminophosphorylamido ester contains at least one such poly(oxyalkylene) polymer (i.e., is at least a monoester). The hydrocarbyl group contains from 1 to about 30 carbon atoms. Preferably the oxyalkylene units contain from 3 to 4 carbon atoms. The molecular weight of the hydrocarbylpoly(oxyalkylene) alcohol is preferably from about 500 to about 5000. Each poly(oxyalkylene) polymer contains at least about 5 oxyalkylene units preferably 8 to about 100 oxyalkylene units, more preferably about 10–100 units, and most preferably 10 to about 25 such units. In general, the oxyalkylene units may be branched or unbranched. Preferably the poly(oxyalkylene) polymer chain contains at least some $C_3$–$C_5$ oxyalkylene units; more preferably, branched $C_3$–$C_5$ oxyalkylene units are present in at least sufficient number to render the hydrocarbyl-terminated poly(oxyalkylene) ester soluble in the lubricating oil composition of the present invention. The branched oxyalkylene units can include oxyalkylene units having the aforementioned $C_4$–$C_{30}$ predominantly straight-chain alkyl substituent. This solubility condition is satisfied if the ester is soluble in hydrocarbons of lubricating viscosity, i.e., about 35–50,000 SUS, at 100° F., at least to the extent of about 0.01% by weight. A poly(oxyalkylene) polymer chain composed of branched $C_4$ oxyalkylene units in at least sufficient amount to effect solubility in the lube composition is most preferred. The structures of the $C_3$–$C_5$ oxyalkylene units are any of the isomeric structures well known to the organic chemist, e.g., n-propylene, —$CH_2CH_2CH_2$—; isopropylene, —$CH(CH_3)CH_2$—; n-butylene, —$CH_2CH_2CH_2CH_2$—; sec.-butylene, —$CH(CH_2CH_3)CH_2$—; tert.-butylene, —$C(CH_3)_2CH_2$—; disec.-butylene, —$CH(CH_3)CH(CH_3)$—; isobutylene, —$CH_2CH(CH_3)CH_2$—; etc. The preferred poly(oxyalkylene) compounds are composed, at least in part, of the branched oxyalkylene isomers, particularly oxy(sec.-butylene) units which are obtained from 1,2-butylene oxide.

The hydrocarbyl moiety (R—) which terminates the poly(oxyalkylene) chain contains from 1 to about 30 carbon atoms, and is generally derived from the monohydroxy compound (ROH) which is the initial site of the alkylene oxide addition in the polymerization reaction. Such monohydroxy compounds are preferably aliphatic or aromatic alcohols of from 1 to about 30 carbon atoms, more preferably an alkanol or an alkylphenol, e.g., alkylphenol wherein the alkyl is a straight or branched chain of from 1 to about 24 carbon atoms. One such preferred alkyl group is obtained by polymerizing propylene to an average of 4 units and has the common name of propylene tetramer. This compound may be termed either an alkylphenylpoly(oxyalkylene) alcohol or a polyalkoxylated alkylphenol.

A preferred class of hydrocarbyl poly(oxyalkylene) aminophosphorylamidoesters are monoesters or diesters of an aminophosphoramidic acid $R^1R^2N$-$P(O)(OH)_2$, wherein the aminoamide moiety, $R^1R^2N$—, contains from 1 to about 11 amine nitrogen atoms and from 2 to about 40 carbon atoms; $R^1$ and $R^2$ being the same or different monovalent aminocarbyl groups and $R^1$ or $R^2$ may be hydrogen. Such aminoamide moieties are illustrated by $H_2NC_2H_4NH$—, $H$-($HNC_2H_4$-$)_mN$-H—wherein m is an integer from 1 to 11, $H_2NC_3H_6NH$—, etc, and any aminoamide moiety derived from the aforementioned polyamines and substituted polyamines. Such hydrocarbylpoly(oxyalkylene) aminophosphorylamido esters may be represented as $R^1R^2N$—$P(O)(OH)_a[$-($OR'$-$)_nOR]_b$ wherein a and b are integers such that a+b=2 but b≧1 and n is an integer from about 5 to 100. R is a hydrocarbyl group of from 1 to 30 carbon atoms and —OR'— is selected from among the aforementioned oxyalkylene units.

Another preferred class of hydrocarbylpoly(oxyalkylene) aminophosphorylamido esters are monoesters of the aminophosphordiamidic acid $(R^1R^2N$-$)_2P(O)(OH)$, which are representable as $(R^1R^2N$-$)_2P(O)$-($OR'$)$_n OR$.

Still another preferred class of hydrocarbylpoly(oxyalkylene) aminophosphorylamido esters are monoesters of the aminophosphorcyclodiamidic acid

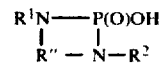

wherein the aminoamide moiety

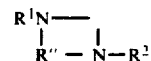

contains up to 10 amine nitrogen atoms and 40 carbon atoms, $R^1$ and $R^2$ are selected from hydrogen and 1–40 hydrocarbyl or aminohydrocarbyl groups derived from the aforementioned polyamine or substituted polyamine components, and R" is ethylene or propylene. Such hydrocarbylpoly(oxyalkylene) aminophosphorylamido esters may be represented as

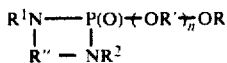

$$R^1N\text{------}P(O)\text{-}(OR')_n\text{-}OR$$
$$\phantom{R^1N------P(O)}|\phantom{(OR')_n}|$$
$$\phantom{R^1N------}R''-NR^2$$

Preferred Method of Preparation

The hydrocarbylpoly(oxyalkylene) aminophosphorylamido esters are preferably prepared in two steps. The first step of the process is the esterification of phosphoryl trichloride, $POCl_3$. Typically, polyether alcohol:$POCl_3$ mol ratios of 2.3:1 to 0.3:1 are used, and ratios of about 1:1 to 0.3:1 are preferred. The use of a three-fold excess of phosphoryl trichloride improved the product yield. The esterification should be effected in an anhydrous environment with or without an inert solvent, preferably without solvent. The esterification is generally conducted at 40°–50° C., for 2–30 hours, preferably 12–30 hours. $POCl_3$ is poured into the stirred polyether alcohol. Evaporation of the solvent, if any, after the reaction, provides the ester, which is generally a mixture of the monoester and the diester. If the reaction is effected under the aforesaid conditions, the triester is practically not formed. In a second step, the chlorophosphoryl ester is reacted with a polyamine. The reaction with the polyamine is preferably effected under the following conditions: Typically, polyamine and ester are contacted in a mol ratio of about 1.5–5:1, preferably about 5:1; polyamine is added as quickly as possible to the chlorophosphoryl ester and an exotherm is observed; after addition is complete the reaction mixture is stirred 2–30 hours at 25°–150° C., usually 25°–50° C. In general, no solvent is used in this reaction, but when a three-fold excess of $POCl_3$ is used, an aromatic solvent such as toluene may be used; the solvent is evaporated before the addition of amine. The final product is extracted with hot n-butyl alcohol and water, stripped and azeotroped with toluene. The product is a mixture containing the aforementioned aminophosphorylamido diesters and monoesters. Among the monesters may be included the aforementioned monoesters of a phosphorcyclodiamidic acid. The latter monoesters are formed when the polyamine is an ethylene- or propylenepolyamine, e.g., ethylenediamine, diethylenetriamine, propylenediamine, etc.

EXAMPLES

Example 1

The reaction was carried out in dry glassware under nitrogen. Phosphorus oxychloride, $P(O)Cl_3$, (10.6 ml, 0.12 mol) was placed in the flask and a monobutylpoly(oxypropylene) alcohol of average molecular weight about 1300 (300 g, 0.23 mol) was poured into the flask. The reaction was stirred overnight at 30°–40° C. After cooling to room temperature, diethylenetriamine (DETA) (50 ml, 0.46 mol) was added all at once in one step. The pot temperature rose to 90° C. and the reaction was stirred for 4 hours. The product mixture was extracted into n-butanol and washed 6 times with hot water. The solvent was removed using a rotary evaporator and 287 g of a viscous liquid of average molecular weight 1815 was obtained containing 0.44% basic nitrogen, 0.73% nitrogen and 0.67% phosphorus.

Example 2

The following reaction was carried out under anhydrous conditions. An oleylpoly(oxypropylene) alcohol of average molecular weight about 1550 (199 g, 0.13 mol) was azeotroped with toluene to remove water immediately prior to use. The alcohol was stirred and $POCl_3$ (13 ml, 0.14 mol) was added in one step. The mixture was stirred for 16 hours at temperatures between 40° and 50° C. Diethylenetriamine (DETA) (76 ml, 0.7 mol) was added to the stirred solution. An exotherm was noted and the pot temperature rose to 120° C. The product mixture was extracted into n-butanol and washed 8 times with hot water. The solvent was removed using a rotary evaporator, and 175 g of a viscous liquid of average molecular weight 2265 was obtained. The product contained 0.42% basic nitrogen, 1.10% nitrogen and 0.94% phosphorus.

Example 3

The following reaction was carried out in dry glassware under nitrogen. Alkylphenylpoly(oxybutylene) alcohol of average molecular weight about 1480 wherein the alkylphenyl is propylene tetramer alkylated phenyl (600 g, 0.4 mol) was stirred while phosphoryl chloride (37 ml, 0.4 mol) was added. The reaction mixture was heated to 40°–50° C. and stirred for 26 hours, then heated to 80° C. for 2 hours. After cooling the reaction mixture to 50° C., triethylenetetraamine (TETA) was added (296 g, 2.0 mol). The first 50 ml was added all at once, and the temperature rose to 95° C. Thereafter, addition was continued at a rate sufficiently slow to prevent the pot temperature from rising any higher. The pot temperature had dropped to 60° C. by the time all the TETA had been added. The reaction mixture was stirred at room temperature for 2 days. The product was extracted into 3 liters of n-butanol and washed 5 times with 300 ml aliquots of hot water. The solvent was removed on the rotary evaporator. A yield of 563 g of a viscous liquid of average molecular weight 1486 was obtained. The product contained 0.38% basic nitrogen, 0.75% nitrogen and 0.54% phosphorus.

A summary of the analytical data on various preparations of the product of this invention appears in Table I. Also included in Table I is an estimate of the mol percent of cyclodiamide (i.e. the monoester of aminophosphorcyclodiamidic acid) in the product. Using these particular polyamines, i.e., ethylene and propylene polyamines, the monoester of aminophosphordiamidic acid (as opposed to the monoester of aminophosphorcyclodiamidic acid) is expected to appear in the product in significant amounts only when the intermediate chlorophosphoryl ester is added dropwise to the polyamine. In all the examples of Table I, however, the amine was added to the chlorophosphoryl ester (preferably contacted all at once, or as rapidly as possible consistent with the exothermic nature of the reaction), so little of the monoester of aminophosphordiamidic acid, which is not a cyclodiamide, is believed to have formed. The total nitrogen to basic nitrogen ratio can be used to determine whether or not the cyclodiamide is a major component of the nitrogen-containing active fraction of the product. If the amount of diamide other than cyclodiamide is assumed to be negligible, one can estimate the molar percentage of cyclodiamide in the active fraction. For example, when diethylenetriamine is used as the polyamine, one expects a total-to-basic nitrogen ratio of 3 if the cyclodiamide were formed exclusively, and a ratio of 1.5 if the monoamide were formed exclusively. The data in Table I indicate that the dispersancy is better when the percentage of cyclodiamide in the active fraction is large. The dispersancy of most of the esters is very good, for example, a commonly used ashless dispersant, polybutene succinimide, has a dispersancy value in the LDT of Table I of 200 ppm.

The preferred products of this invention have been described with a view to providing the most effective lubricating oil composition for improved lubricity and other properties. While improved lubricity is a major achievement of the compounds of the invention, other desirable properties such as resistance to oxidation and corrosion, extreme-pressure lubrication, and anti-wear are imparted to lubricating oil compositions. Other desirable properties or undesirable problems of lubricating oil compositions include sludge formation, detergency and dispersancy, viscosity, emulsification, rust, compatibility and interaction with fuel and other additives, which must be considered in the practice of the present invention.

Lubricating Oil Compositions

The lubricating oil compositions of the invention are useful for lubricating internal combustion engines. The lubricating oils not only lubricate the engine, but, because of their dispersancy properties, help maintain a high degree of cleanliness of the lubricated parts.

Suitable lubricating oils which can be used to prepare a lubricating oil composition or concentrate of this invention are oils of lubricating viscosity derived from petroleum or synthetic sources. The oils can be paraffinic, naphthenic, halo-substituted hydrocarbons, synthetic esters, polyethers, alkylbenzenes, or combinations thereof. Oils of lubricating viscosity have viscosities in the range of 35 to 50,000 SUS at 100° F., and more usually from about 50 to 10,000 SUS at 100° F. The amount of the aminophosphorylamido ester of this invention which is incorporated into the lubricating oil to provide the effective amount necessary for dispersancy varies widely with the particular aminophosphorylamido ester used as well as the use intended for the lubricating oil composition. Other conventional additives which can be used in combination with the poly(oxyalkylene) aminophosphorylamido esters of this invention include ashless dispersants such as the type disclosed in U.S. Pat. Nos. 3,172,892, 3,219,666, 3,381,022; neutral and basic calcium, barium and magnesium petrosulfonates or alkylphenates; oxidation inhibitors, antifoam agents, viscosity index improvers, pour-point depressants, and the like, such as chlorinated wax, benzyldisulfide, sulfurized sperm oil, sulfurized terpene; phosphorus esters such as trihydrocarbon phosphites and phosphates; metal thiocarbamates such as zinc dioctyldithiocarbamate; metal phosphorus dithioates such as zinc dioctylphosphorodithioate; polyisobutene having an average molecular weight of 100,000; etc.

In general, the lubricating oil compositions will contain from about 0.001 to about 20 weight percent of said oil-soluble aminophosphorylamido ester. More usually, the lubricating oil composition of the invention will contain from about 0.01 to about 10 weight percent of the aminophosphorylamido ester, and more usually from about 0.5 to about 8 weight percent of the aminophosphorylamido ester.

In a second embodiment of this invention, lubricating oil additive concentrates are provided comprising from about 90 to about 20 weight percent of an inert stable oleophilic solvent such as an oil of lubricating viscosity and from about 10 to about 80 weight percent of the poly(oxyalkylene) aminophosphorylamido ester of this invention. Typically, the concentrates contain sufficient diluent to make them easy to handle during shipping and storage. Preferably, the diluent is an oil of lubricating viscosity so that the concentrate may be readily mixed with lubricating oils to prepare lubricating oil compositions. Suitable lubricating oils which can be used as diluents typically have viscosities in the range from about 35 to about 1000 Saybolt Universal Seconds (SUS) at 100° F., although any oil of lubricating viscosity can be used.

TABLE I

| Analytical Data on Hydrocarbylpoly(oxyalkylene) aminophosphorylamido esters | | | | | | | |
|---|---|---|---|---|---|---|---|
| Alcohol (ROH), Amine | ROH:POCl₃ Charge Ratio | Product Avg. MW | Basic N. % | N. % | P. % | LDT,[1] ppm | Cyclodiamide,[8] Mol % |
| UCON LB 385,[2] DETA[3] | 2.3 | 1637 | 0.40 | 0.58 | 0.55 | 400 | 0 |
| UCON LB 385, DETA | 2.1 | 1735 | 0.44 | 0.73 | 0.67 | 200–400 | 10 |
| UCON LB 385, TETA[4] | 2.3 | 1565 | 0.36 | 0.55 | 0.44 | 400–800 | 15 |
| UCON LB 625,[5] TETA | 0.8 | 1700 | 0.34 | 0.54 | 0.32 | 200–400 | 6 |
| UCON LB 625, TETA | 0.8 | 1843 | 0.86 | 1.24 | 0.58 | 100 | 20 |
| UCON LO 500,[6] DETA | 0.9 | 2032 | 0.42 | 1.10 | 0.94 | 10–20 | 75 |
| UCON LO 500, TETA | 0.9 | 1836 | 0.64 | 1.23 | 0.71 | 10–20 | 90 |
| Alkylphenol BuO,[7] TETA | 1.0 | 1486 | 0.38 | 0.75 | 0.54 | 50 | 95 |
| Alkylphenol BuO, TETA | 0.3 | 1470 | 0.51 | 1.07 | 0.77 | 50 | about 100 |

[1]LDT = Laboratory Dispersancy Test. The numbers represent the ppm of additive required to suspend a given volume of chloroform-soluble engine sludge in gasoline for 20 minutes.
[2]n-Butylpoly(oxypropylene) alcohol of MW about 1300. UCON is a trade name of Union Carbide Corp.
[3]Diethylenetriamine.
[4]Triethylenetetraamine.
[5]Similar to LB 385 but of MW about 1800.
[6]Oleylpoly(oxypropylene) alcohol of MW about 1550.
[7]Alkylphenylpoly(oxybutylene) alcohol of MW about 1450, derived from propylene tetramer phenol.
[8]Mol percent of hydrocarbylpoly(oxyalkylene) monoester of aminophosphorcyclodiamidic acid in the product.

The effectiveness of lubricating oil additives of the present invention as agents tending to improve the lubricity of lubricating oil compositions at lower levels of phosphorus is shown in the Falex Extreme Pressure Test (ASTM D-3233) results of Table II.

TABLE II

| | Falex EP Results | | |
|---|---|---|---|
| Additive | % in Lubricating Oil | mmol p/ kg Oil | Seizure Load, Lb |
| None | — | — | 950,1000[5] |
| PB Succinimide[1] | 4.0 | — | 875,925,925[6] |
| TETA ester[2] | 5.35 | 9 | 1350,1400,1650[6] |
| ZTDP[3] | 3.5 | 36 | 1200,1200[5] |

TABLE II-continued

| | Falex EP Results | | |
|---|---|---|---|
| Additive | % in Lubricating Oil | mmol p/ kg Oil | Seizure Load, Lb |
| ZTDP[4] | 1.25 | 36 [5] | 1050,1100,1200[6] |

[1]Polyisobutenylsuccinimide tetraethylenepentamine (average molecular weight about 1000).
[2]Alkylphenylpoly(oxybutylene)aminophosphorylamido ester from triethylenetetraamine.
[3]Zinc bis(polypropylenephenyl)dithiophosphate.
[4]Zinc dioctyldithiophosphate.
[5]Two tests.
[6]Three tests.

Although many specific embodiments of the invention have been described in detail, it should be understood that the invention is to be given the broadest possible interpretation within the terms of the following claims.

What is claimed is:

1. The compound which is a hydrocarbylpoly(oxyalkylene) aminophosphorylamido ester; said compound being the amide of a polyamine and the ester of a hydrocarbylpoly(oxyalkylene) alcohol, wherein said hydrocarbyl group contains from 1 to about 30 carbon atoms and said polyamine contains from 2 to about 12 amine nitrogen atoms and from 2 to about 40 carbon atoms.

2. The compound which is a hydrocarbylpoly(oxyalkylene) monoester or diester of an aminophosphoramidic acid

$$R^1N-P(O)(OH)_2$$

wherein the aminoamide moiety of said acid, $R^1R^2N-$, contains from 1 to about 11 amine nitrogen atoms and from 2 to about 40 carbon atoms, $R^1$ and $R^2$ are the same or different monovalent aminohydrocarbyl groups and $R^1$ or $R^2$ may be hydrogen, and the hydrocarbyl group in said hydrocarbylpoly(oxyalkylene) moiety contains from 1 to about 30 carbon atoms.

3. The compound which is a hydrocarbylpoly(oxyalkylene) monoester of an aminophosphordiamidic acid

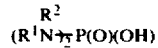
$$(R^1N)_2P(O)(OH)$$

wherein the aminoamide moiety of said acid, $R^1R^2N-$, contains from 1 to about 11 amine nitrogen atoms and from 2 to about 40 carbon atoms, $R^1$ and $R^2$ are the same or different monovalent aminohydrocarbyl groups and $R^1$ and $R^2$ may be hydrogen, and the hydrocarbyl group in said hydrocarbylpoly(oxyalkylene) moiety contains from 1 to about 30 carbon atoms.

4. The compound which is a hydrocarbylpoly(oxyalkylene) monoester of an aminophosphorcyclodiamidic acid,

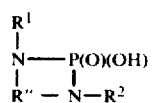

wherein the aminoamide moiety of said acid,

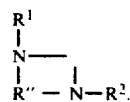

contains up to about 10 amine nitrogen atoms and from 2 to about 40 carbon atoms, wherein $R''$ is ethylene or propylene, $R^1$ and $R^2$ are the same or different monovalent groups selected from hydrogen, $C_1-C_{40}$ hydrocarbyl or aminohydrocarbyl groups, and the hydrocarbyl group in said hydrocarbylpoly(oxyalkylene) moiety contains from 1 to about 30 carbon atoms.

5. The compound of claim 1 wherein said hydrocarbylpoly(oxyalkylene) aminophosphorylamido ester is the monoester having a molecular weight from about 600 to 5000.

6. The compound of claim 1 wherein said hydrocarbylpoly(oxyalkylene) aminophosphorylamido ester is the diester having a molecular weight from about 1000 to 10,000.

7. The compound of claims 1, 2, 3 or 4 wherein said hydrocarbylpoly(oxyalkylene) group contains oxyalkylene units selected from $C_2-C_5$ oxyalkylene units, including branched-chain oxyalkylene units having $C_4-C_{30}$ predominantly straight-chain alkyl substituents.

8. The compound of claim 7 wherein said poly(oxyalkylene) moiety contains at least 5 oxyalkylene units.

9. The compound of claims 1, 2, 3 or 4 in which said hydrocarbyl group is an alkylphenyl group.

10. The compounds of claims 1, 2, 3 or 4 in which said oxyalkylene units are oxybutylene units.

11. The compound of claim 1 wherein said polyamine is selected from ethylenediamine, polyethylenepolyamine, propylenediamine and polypropylenepolyamine.

12. A lubricating oil composition comprising a major amount of an oil of lubricating viscosity, and a minor amount of the compound of claims 1, 2, 3 or 4, wherein said oxyalkylene units are selected from $C_2-C_5$ oxyalkylene units including branched-chain oxyalkylene units having $C_4-C_{30}$ predominantly straight-chain alkyl substituents, wherein at least a sufficient number of said oxyalkylene units are branched-chain oxyalkylene units to render said ester soluble in said lubricating oil composition.

13. A concentrate comprising an inert stable oleophilic organic solvent and from 10 to 80 weight percent of the compound of claims 1, 2, 3 or 4.

* * * * *